United States Patent [19]
Whitaker et al.

[11] 3,963,025
[45] June 15, 1976

[54] OCULAR DRUG DELIVERY DEVICE

[75] Inventors: Gordon W. Whitaker, Palo Alto; Yigal Gad, Mountain View, both of Calif.

[73] Assignee: Alza Corporation, Palo Alto, Calif.

[22] Filed: June 2, 1975

[21] Appl. No.: 582,948

Related U.S. Application Data

[63] Continuation-in-part of Ser. No. 505,629, Sept. 16, 1974, abandoned, which is a continuation of Ser. No. 423,203, Dec. 10, 1973, abandoned, which is a continuation-in-part of Ser. No. 350,062, April 11, 1973, abandoned.

[52] U.S. Cl. .................... 128/260; 128/268
[51] Int. Cl.² .................................... A61M 31/00
[58] Field of Search ........................... 128/260, 268

[56] References Cited
UNITED STATES PATENTS

| | | | |
|---|---|---|---|
| 3,626,940 | 12/1971 | Zaffaroni | 128/260 |
| 3,630,200 | 12/1971 | Higochi | 128/260 |
| 3,828,777 | 8/1974 | Ness | 128/260 |

*Primary Examiner*—Aldrich F. Medbery
*Attorney, Agent, or Firm*—Thomas E. Ciotti; Paul L. Sabatine; Edward L. Mandell

[57] ABSTRACT

Ocular drug delivery device comprising a bioerodible body of polymeric material sized and shaped for insertion in either conjunctival cul-de-sac that have improved retention in the eye. The devices have a stiffness and resistivity to bending manifested by a centroidal unsupported bending angle of less than 40°, preferably less than 20°, during the drug dispensing lifetime of the device.

8 Claims, 3 Drawing Figures

OCULAR DRUG DELIVERY DEVICE

CROSS-REFERENCE TO RELATED APPLICATIONS

This application is a continuation-in-part of copending application Ser. No. 505,629 filed Sept. 16, 1974 and now abandoned, which in turn is a continuation of application Ser. No. 423,203 filed Dec. 10, 1973 and now abandoned, which in turn is a continuation-in-part of application Ser. No. 350,062 filed Apr. 11, 1973 and now abandoned. The parent applications are assigned to the same assignee as this application.

BACKGROUND OF THE INVENTION

1. Field of the Invention

This invention relates to a bioerodible ocular insert for dispensing drugs to the eye that has improved retention in the eye.

2. Description of the Prior Art

Ocular inserts represent a significant advance in the therapy of eye disease. Raher than periodically treating the eye as practiced in the prior art with medication in liquid or ointment form which is rapidly removed from the eye surface by tears, ocular inserts provide a useful sustained release of drug to the eye for a prolonged period of time. Bioerodible ocular inserts are described in Belgian Pat. No. 788,575 dated Sept. 29, 1972 (corresponds to German Offen. P2243986 published Mar. 29, 1973 and U.S. application Ser. No. 179,129 filed Sept. 9, 1971), U.S. Pat. No. 3,811,444 issued May 21, 1974, and U.S. application Ser. No. 544,808 filed Jan. 28, 1975, all assigned to the same assignee as this application. Said patents, publication, and applications are herein expressly incorporated by reference both to illustrate the background against which the present invention was made and to set out examples of the type of ocular insert to which the present invention applies.

Briefly, these ocular inserts act as drug dispensers, remaining in and slowly releasing drug to the eye over prolonged periods of time. The inserts are fabricated of flexible polymeric materials that are biologically inert, non-allergenic, and bioerodible in the environment of the eye. They comprise a body having a size and shape adapted for insertion and wearing in either cul-de-sac. Once placed in either culde-sac, it remains in the eye, releasing drug until either:

1. it is removed,
2. its supply of drug is exhausted,
3. it erodes away, or
4. it is expelled and lost from the ocular cavity.

Any of the first three fates for an ocular device are acceptable since their times of occurence are predictable. The patient will, or at least should, know that the drug is, or is not, being delivered to the eye. If the ocular device is removed, obviously, no drug is thereafter administered. If the drug supply is exhausted or the device has eroded (both events being tied to the stated life of the devices) no drug is thereafter delivered.

The fourth fate or an ocular device, expulsion, must be prevented during the prescribed therapy time. Such expulsion presented a statistically significant problem in the case of prior bioerodible ocular inserts. If involuntary expulsion occurs, the patient may not even know when expulsion has occurred, since ocular inserts are generally so comfortable that their presence or absence in the ocular cavity is not readily noted. Thus, it is possible that after expelling its ocular insert, an eye might go for seriously long periods without needed medication. This would negate one of the primary advantages of an ocular insert, which is controlled continuous medicating of the eye, and potentially, as a result of patient reliance of the ocular device coupled with a failure to check for the presence of the device, could lead to prolonged periods without medication.

It can therefore be seen that a discovery which would improve the eye's retention of ocular inserts and eliminate to any major extent the unpredictable expulsion or ejection of bioerodible ocular inserts from the ocular cavity would indeed be beneficial. The present invention does this.

SUMMARY OF THE INVENTION

We have now found that a bioerodible ocular insert's retention in the eye may be correlated to the insert's flexibility throughout the therapy period, which flexibility is changing continuously due to the physical property changes or bioerosion of the insert. We also found that prior bioerodible ocular inserts were apparently being expelled involuntarily because they become too flexible to be retained in the eye. Accordingly, our invention is an improvement in a sustained release ocular drug delivery device comprising a flexible body formed of a bioerodible polymeric material that is sized and shaped for insertion in a cul-de-sac of the eye and contains a drug, the improvement being that the body has a stiffness and resistivity to bending manifested by a centroidal unsupported bending angle of less than 40°, preferably less than 20°, throughout the drug dispensing lifetime of the device.

DETAILED DESCRIPTION OF THE INVENTION

The ocular inserts to which this invention apply can be fabricated in any convenient and comfortable shape for placement in the cul-de-sac. It is important, however, that the insert have no sharp, jagged, or rough edges which can irritate the sensitive tissues of the eye and that they be sufficiently flexible at all times to be worn comfortably in the eye. The marginal outline of the ocular inserts can be triangular, oval, circular, ring, annular, reniform, square, ellipsoid, bean-shaped, rectangular, or any other symmetrical or unsymmetrical shape. In cross section, it can be concavo-convex, rectangular, etc. Dimensions of the inserts can vary widely. The lower limit on the size of the insert is governed by the amount of the particular drug to be applied to the eye and surrounding tissues to elicit the desired pharmacologic response, as well as by the smallest sized insert which conveniently can be inserted and removed fromthe eye. The upper limit on the size of the inserts is governed by the limited space within the cul-de-sac that conveniently and comfortably can be filled with an ocular insert. Typically, the ocular insert is 3 to 20 mm in length, 1 to 9 mm in width, and 0.05 to 1 mm in thickness. Preferably it is ellipsoidal in shape and about 8 × 5 × 0.5 mm in size.

The ocular inserts comprise a polymer body containing a drug, such as a polymeric matrix with the drug dispersed therethrough. Drug can be incorporated in a polymeric matrix in many ways, for instance by adding the drugs to the monomers prior to polymerization; adding the drug to the fluidized polymer, forming and setting or by impregnating the polymeric material, either before or after shaping to the form of the ocular inserts, with the drug. Drug is released from such ocular inserts by passing from the body of polymeric material at a gradual rate and/or by having encapsulating polymer gradually disintegrate and release entrapped drug. The devices so prepared can be used in animal or human eyes.

Figure 1:
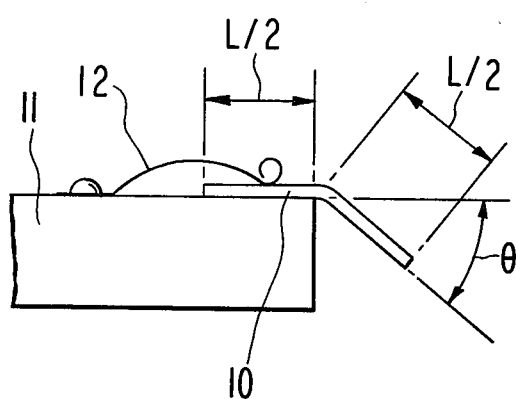
FIGS. 1 and 2 are diagramatic, elevational views of an ocular insert undergoing a test to determine stiffness and resistivity to bending by measuring its centroidal unsupported bending angle.

The ocular inserts of the invention have a stiffness and resistivity to bending as manifested by a centroidal, unsupported bending angle, as determined by the test described herein, of less than 40°, that is 0° – 40°, preferably at least 20°, that is 0° – 20°, throughout the drug dispensing lifetime of the insert. The centroidal unsupported bending angle is the degree of bending of the insert body that is observed when it is placed in a position with a portion of its mass supported and the remainder of its mass unsupported, the line delineating said portion and said remainder passing through the centroid of the body. As indicated by the above stated dimensions, the inserts will normally be thin bodies with one of the two remaining dimensions elongated relative to the other. In determining the centroidal unsupported bending angle for such bodies said line should traverse the elongated dimension. For instance, in a thin, elliptical body, the line would be the minor axis of the ellipse. For symmetrical bodies that line is a center line and half the body is supported and the other half is unsupported. The centroidal unsupported bending angle for such symmetrical bodies is herein called the "half length unsupported bending angle." The determination of the half length bending angle of a flat, elliptical ocular insert 10 is depicted in FIG. 1. In FIG. 1 insert 10 having a known longest dimension L is so placed on the horizontal surface of a block 11 that half of device 10 is supported by the horizontal top surface of block 11 and half of device 10 is hanging over the edge. Device 10, may if desired, be held in place by temporary means, such as clip 12. The half length bending angle, defined as θ, is illustrated in FIG. 1. The measurement of θ may be carried out by a variety of methods. In one method, visual measurement of the distance device 10 hangs down is made with a cathetometer or the like and θ then calculated from the relationship.

$$\text{Arcsin}\left(\frac{\text{Distance hanging down}}{L/2}\right) = \theta$$

Figure 2:
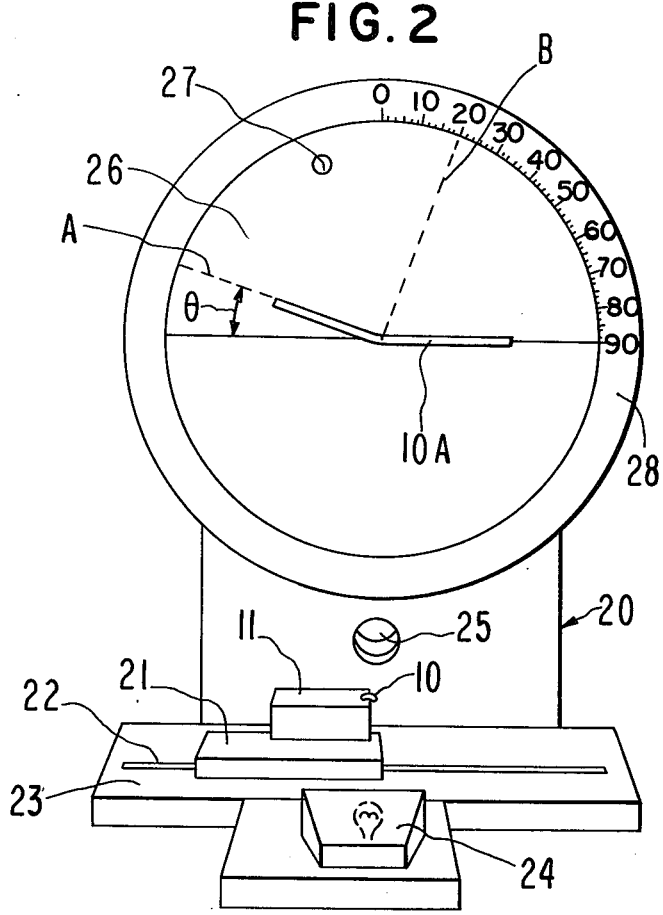

A more accurate determination of θ may be made by direct measurement on an optical comparator such as is marketed by MicroVu Corporation. FIG. 2 illustrates in perspective view, measurement of unsupported bending angle with such a comparator. In FIG. 2 an ocular device 10 is depicted positioned on block 11 with half its longest dimension unsupported. Block 11 is mounted in comparator 20 on stage 21. Stage 21 is movable along track 22 in base 23. A focused beam of light from light source 24 is projected across ocular device 10 and collected in lens 25. This beam of light which now carries an image of device 10 is rear-projected by optics not shown onto rotatable translucent screen 26. Image 10A is a magnification of device 10 which appears on screen 26. Stage 21 is moved to position image 10A in the exact center of screen 26. Screen 26 is rotated by handle 27 until line A on screen 26 corresponds to the bending angle θ of device 10. Line B on screen 26, which is fixed in relation to line A indicates the value for angle θ on a scale on support 28. That is, on the scale, 20 indicates an angle of 20°, 30 a 30° angle, 35 a 35° angle, and so forth.

It should be noted that the measurement of bending angle should be made on the ocular insert when it is wet as a result of contact with a real or simulated ocular environment, since it is the flexibility of the device in the ocular environment which is critical to retention in the ocular environment.

In general the centroidal unsupported bending angle is a function of the composition and geometry of the ocular insert. Either or both of these characteristics may be varied to provide an insert that has a bending angle within the invention. For instance, composition may be varied by changing the polymer chemically or structurally or by adding additives, such as plasticizers, to it. The term "drug dispensing lifetime" is intended to mean the period over which the device provides the prescribed therapy, and the actual period over which the device releases drug may be longer than said lifetime. Usually said lifetime will be in excess of one-half day and more usually at least one day. Dispensing lifetimes of one week are common.

The correlation of retention to flexibility is clearly shown in the following examples:

EXAMPLE 1 plurality of elliptical flat ocular inserts are prepared. They are 0.26 mm thick when dry and have 11.9 mm and 4.2 mm major and minor axes. They are fabricated of micronized hydrocortisone acetate in a glycerine-plasticized cross-linked gelatin matrix. When placed in tear fluid, they swell slightly to a thickness of about 0.51 mm.

Figure 3:
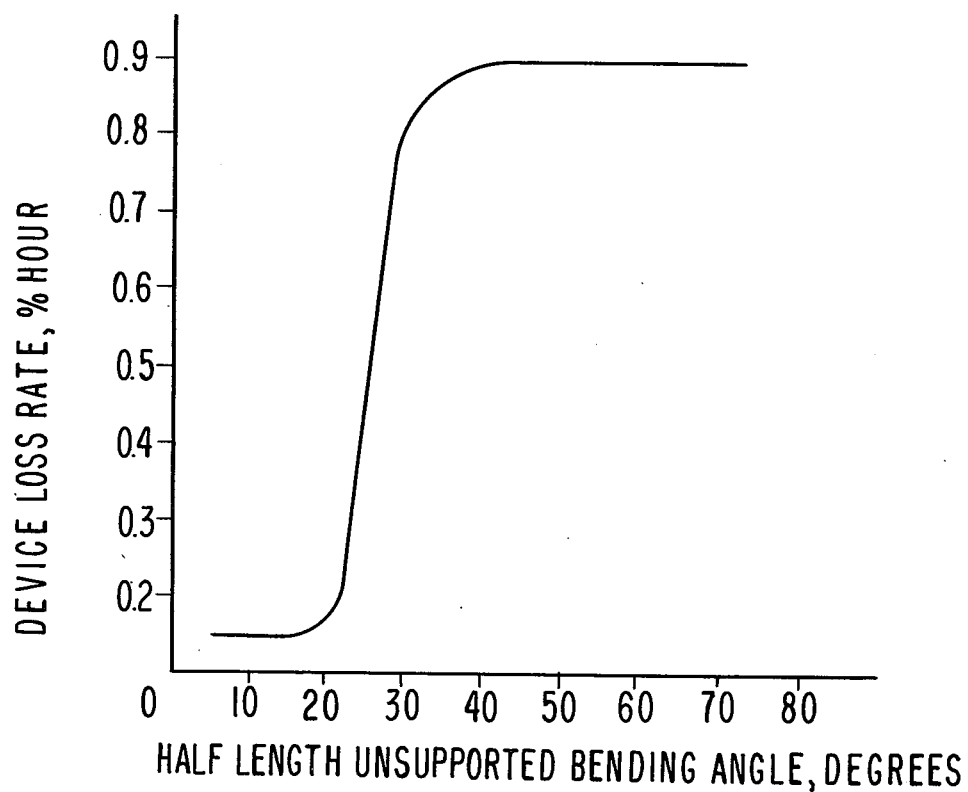
FIG. 3 is a graphic illustration of ocular insert retention as a function of the half length unsupported bending angle.

These ocular devices initially exhibit a half length unsupported bending angle which is less than 20°, usually 0° – 20°. They are inserted in a plurality of eyes, one insert per eye. As time passes, drug is continuously released to the eyes. Periodically, sample groups of devices are removed and their half length unsupported bending angles mesured. Also, careful watch is maintained for expulsion of devices from eyes. Over the first 50 hours of use the bending angle remains substantially constant at less than 5°. There is an occasional device expulsion, but the rate remains a low 0.155 – 0.160 loss per hour. At such a loss rate, only about 15 of the total ocular devices would be expelled in a week's wearing. After about 50 hours, however, a marked change occurs in flexibility and retention (in this case because of breakdown in chemical cross-links in the gelatin). Bending angle increases from 0° – 5° to 10°, 15°, 20°, 25°, 30°, 35° and 40° and on up to nearly 90°. Simultaneously the rate of device expulsion increases more than five-fole to 0.88 – 0.92 loss/hour. This relationship is illustrated in FIG. 3. Other properties are measured, such as area and weight; none is seen to change significantly during the period when expulsion icreases.

The rate of expulsion at the higher bending angles above 40°, is unacceptble. Virtually all the devices are lost in a week's wearing.

EXAMPLE 2

The experiment of Example 1 is repeated with one change, a more tightly cross-linked gelatin is substituted into the device. The initial bending angle is 0° – 5° with use, this angle does not increase beyond 20° in the first 120 hours of testing. Throughout the first 120 hours of the test period, the rate of device expulsion remains substantially constant at about 0.1 – 0.15 expulsion/hour.

EXAMPLE 3

The experiment of Example 1 is repeated several times varying the outline shape of the device among:
 a 4 mm diameter circle,
 a 5 mm diameter circle,
 a 6 mm diameter toroid, and
 a 8 mm by 5 mm ellipse.
All of these devices show marked decreases in retention when their half length free bending angle exceeds 40° during wearing in the eye.

We claim:

1. In a sustained release ocular drug delivery device comprising a flexible body that is formed of a bioerodible polymeric material, sized and shaped for insertion in either cul-de-sac of the eye, and contains a drug, the improvement wherein the body has a stiffness and resistivity to bending manifested by a centroidal unsupported bending angle of less than 40° during its drug dispensing lifetime.

2. The improvement of claim 1 wherein the centroidal unsupported bending angle is less than 20° during said drug dispensing lifetime.

3. The improvement of claim 1 wherein said polymeric material is cross-linked gelatin.

4. The improvement of claim 1 wherein said body is 3 – 20 mm in length, 1 – 9 mm in width and 0.05 – 1 mm in thickness.

5. The improvement of claim 1 wherein the drug dispensing lifetime is in excess of one-half day.

6. The improvement of claim 1 wherein the drug dispensing lifetime is at least one day.

7. The improvement of claim 1 wherein the body is 3 – 20 mm in length, 1 – 9 mm in width and 0.05 – 1 mm in thickness and the drug dispensing lifetime is at least one day.

8. The improvement of claim 7 wherein the polymeric material is cross-linked gelatin.

* * * * *